United States Patent
Cheetham

Patent Number: 5,816,805
Date of Patent: Oct. 6, 1998

[54] DENTAL AMALGAM CAPSULE

[75] Inventor: Jeffery James Cheetham, Bayswater, Australia

[73] Assignee: Southern Dental Industries, Limited, Victoria, Australia

[21] Appl. No.: 752,383

[22] Filed: Nov. 20, 1996

Related U.S. Application Data

[63] Continuation of Ser. No. 470,416, Jun. 6, 1995, abandoned, which is a continuation of Ser. No. 859,379, filed as PCT/AU90/00566 Nov. 23, 1990, abandoned.

[30] Foreign Application Priority Data

Nov. 23, 1989 [AU] Australia .................................. PJ 7528
Mar. 30, 1990 [AU] Australia .................................. PJ 9400

[51] Int. Cl.⁶ ...................................................... A61C 5/04
[52] U.S. Cl. ........................................................... 433/90
[58] Field of Search ................................ 433/80, 89, 90; 604/82, 87, 90, 92; 206/63.5, 219, 222; 222/80, 81, 82, 87, 136, 145

[56] References Cited

FOREIGN PATENT DOCUMENTS

| | | |
|---|---|---|
| 1964770 | 7/1971 | Australia . |
| 1829570 | 11/1974 | Australia . |
| 1459270 | 9/1975 | Australia . |
| 3223771 | 5/1976 | Australia . |
| 8508575 | 3/1977 | Australia . |
| 5709680 | 10/1980 | Australia . |
| 7263487 | 11/1987 | Australia . |

*Primary Examiner*—Nicholas D. Lucchesi
*Attorney, Agent, or Firm*—William H. Holt; William R. Hinds

[57] ABSTRACT

The invention relates to a dental amalgam capsule 10 arranged to contain mercury in a first compartment 16 and dental alloy powder in a second, or mixing, compartment 18, a conduit 28 being provided so that amalgam can be dispensed by a rod 66 directly from the capsule 10 into a cavity in a tooth.

8 Claims, 11 Drawing Sheets

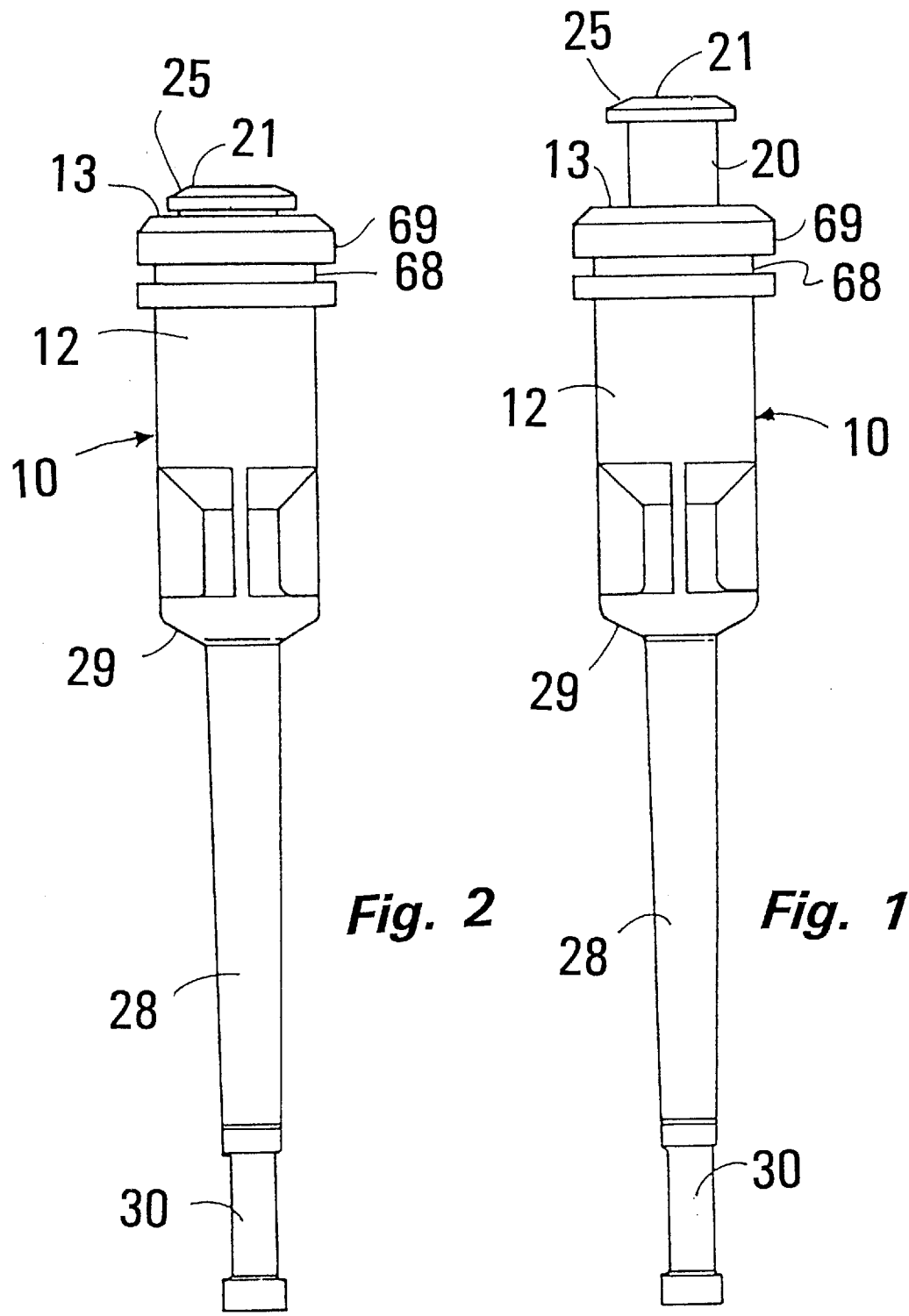

DENTAL AMALGAM CAPSULE

This is a continuation of application Ser. No. 08/470,416 filed Jun. 6, 1995, now abandoned, which is a continuation of Ser. No. 07/859,379 filed May 26, 1992, now abandoned, which was the U.S. national stage of International application No. PCT/AU90/00566 filed Nov. 23, 1990.

The present invention relates to a dental amalgam capsule.

FIELD OF THE INVENTION

Dental amalgam capsules have been known for some time and typically comprise two compartments. One compartment contains dental alloy and the other contains mercury. The components in the compartments are brought together such as by depression of a plunger to rupture a partition. The resulting alloy and mercury mixture is then amalgamated such as by the placement of the capsule into a high speed amalgamator.

A disadvantage of previously known capsules is that once the amalgam has been formed, the capsule has to be opened, and the amalgam has to be manually removed and then placed into a cavity of a tooth to be restored.

This operation requires a dental nurse to empty the amalgam from the capsule into an amalgam well. Then an amalgam carrier is loaded from the amalgam well. The loaded amalgam carrier is handed to the dentist who then injects the amalgam into the tooth cavity. The dentist usually returns the amalgam carrier to the nurse for reloading. This operation may be repeated from 3 to 5 times depending on the size of the amalgam mix.

The above described mode of operation is time consuming and also exposes the dental nurse to unset amalgam with attendant danger of the nurse being exposed to mercury vapour.

In addition, amalgam is often dropped out of the amalgam carrier as the carrier is being handed to the dentist. Also, amalgam carriers are often rendered inoperable after a short working life in that amalgam can work its way into the carrier and cause it to jam. Also the carrier can retain set amalgam from previous operations with the risk that set amalgam can be mixed with fresh amalgam such that a mixture of set and unset amalgam can be placed in a cavity.

SUMMARY OF THE INVENTION

The present invention provides a dental amalgam capsule in which the amalgam can be placed directly into a tooth cavity without the need for prior removal as with previously known devices.

In accordance with one aspect of the present invention there is provided a dental amalgam capsule characterised by comprising a body and a conduit extending from the body, a chamber within the body and the conduit arranged to contain mercury and particulate dental alloy in separated condition, means being provided for enabling the mercury and the particulate dental alloy to contact one another and to be formed into an amalgam, the conduit being of lesser external dimension than the body and having an outlet end.

In accordance with a further aspect of the present invention there is provided an applicator for use with the dental amalgam capsule of the present invention, characterised by comprising a hollow elongated body member having a leading end and a trailing end, a rod extending through the body member, means engaging with the rod to push it towards the leading end in increments and means attached to the rod for pushing amalgam out of the conduit of a said capsule mounted to a leading end of the rod.

BRIEF DESCRIPTION OF THE DRAWINGS

The present invention, will now be described, by way of example, with reference to the accompanying drawings, in which:

FIG. 1 is a side elevation of a dental amalgam capsule in accordance with the present invention in unactivated state and with an amalgam delivery conduit in straight condition;

FIG. 2 is a view similar to FIG. 1 with the amalgam capsule in activated state;

FIG. 10 is a view similar to FIG. 9 showing the condition of the applicator and capsule immediately after dispensing has ceased and the capsule is ready to be disposed of;

DESCRIPTION OF THE INVENTION

Figure 3:
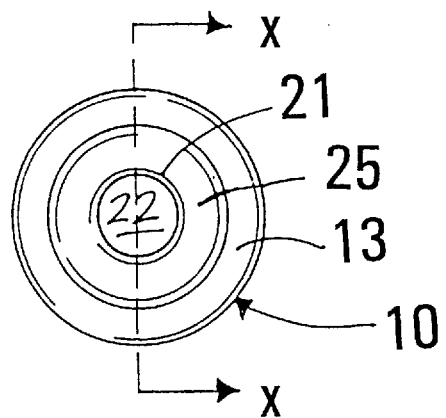
FIG. 3 is a plan view of the capsule of FIGS. 1 and 2.
Figure 4:
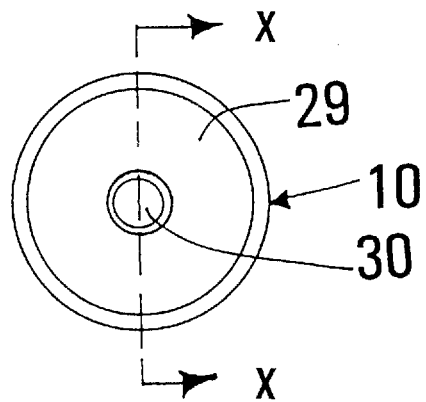
FIG. 4 is an underneath view of the capsule of FIGS. 1 and 2.

In FIGS. 1 to 6 of the accompanying drawings there is shown a dental amalgam capsule 10 comprising a body 12. The body 12 contains a generally cylindrical shaped recess extending from the upper end 13 as seen in FIG. 3. The generally cylindrical shaped recess however tapers inwardly away from the said upper end 13.

Further, the generally cylindrical shaped recess contains a mercury container 14 of complementary outer shape to the internal shape of the said recess. The generally cylindrical shaped recess contains a circumferential groove 15 into which a portion of the mercury container 14 fits such as by deformation so as to prevent the mercury container 14 from moving longitudinally inadvertently.

The capsule 10 contains a chamber formed of first and second compartments to be described, in the unactivated condition of the capsule 10 best seen in FIG. 3.

The mercury container 14 contains a cylindrical first compartment 16 which contains mercury. Inwardly of the inner end of the compartment 16 the chamber is closed off by a thin membrane or partition 17. The partition 17 divides the chamber into the first compartment 16 and a second compartment 18 which also constitutes a mixing chamber. An outer end of the compartment 16 remote from the partition 17 is closed off by a slidably mounted plunger 20. The plunger 20 is in the form of an elongated shaft which fits snugly into the compartment 16. The plunger 20 has an open outer end 21. A longitudinally extending recess 22 extends inwardly from the open end 21. The recess 22 has an inner end which is closed off by a thin membrane 23.

Figure 5:
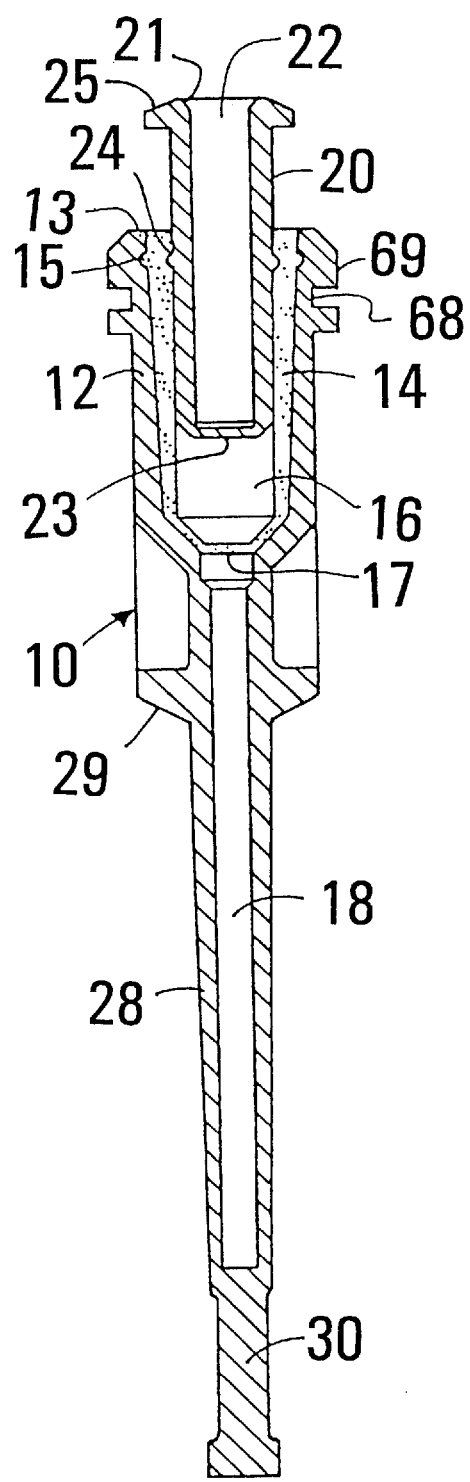
FIG. 5 is a vertical section through the capsule as shown in FIG. 1 along the lines X—X of FIGS. 3 and 4.
Figure 7:
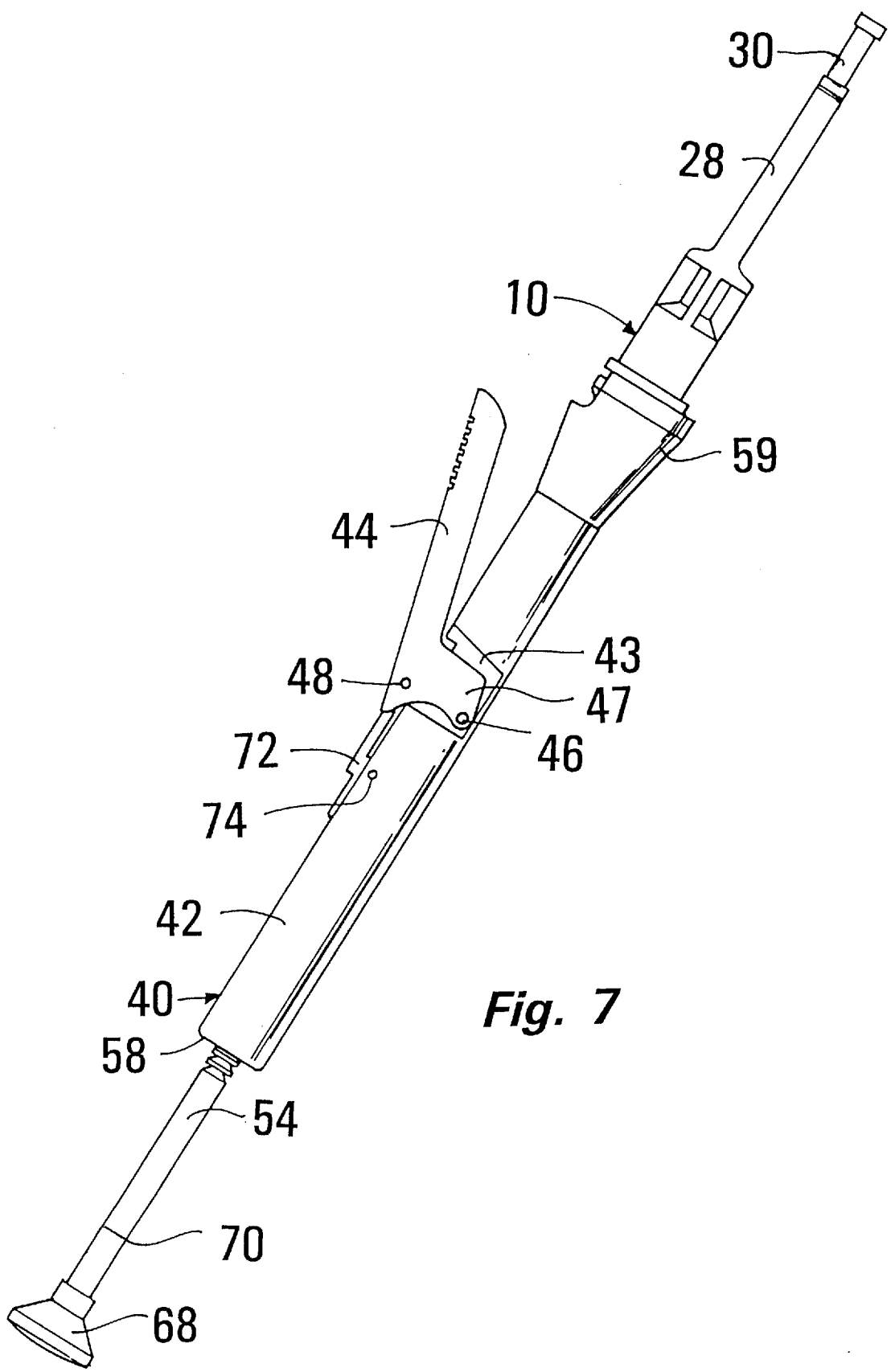
FIG. 7 is a side elevation of an applicator for dispensing amalgam from the capsule of FIGS. 1 to 6, with a capsule of FIGS. 1 to 6 in place.
Figure 8:
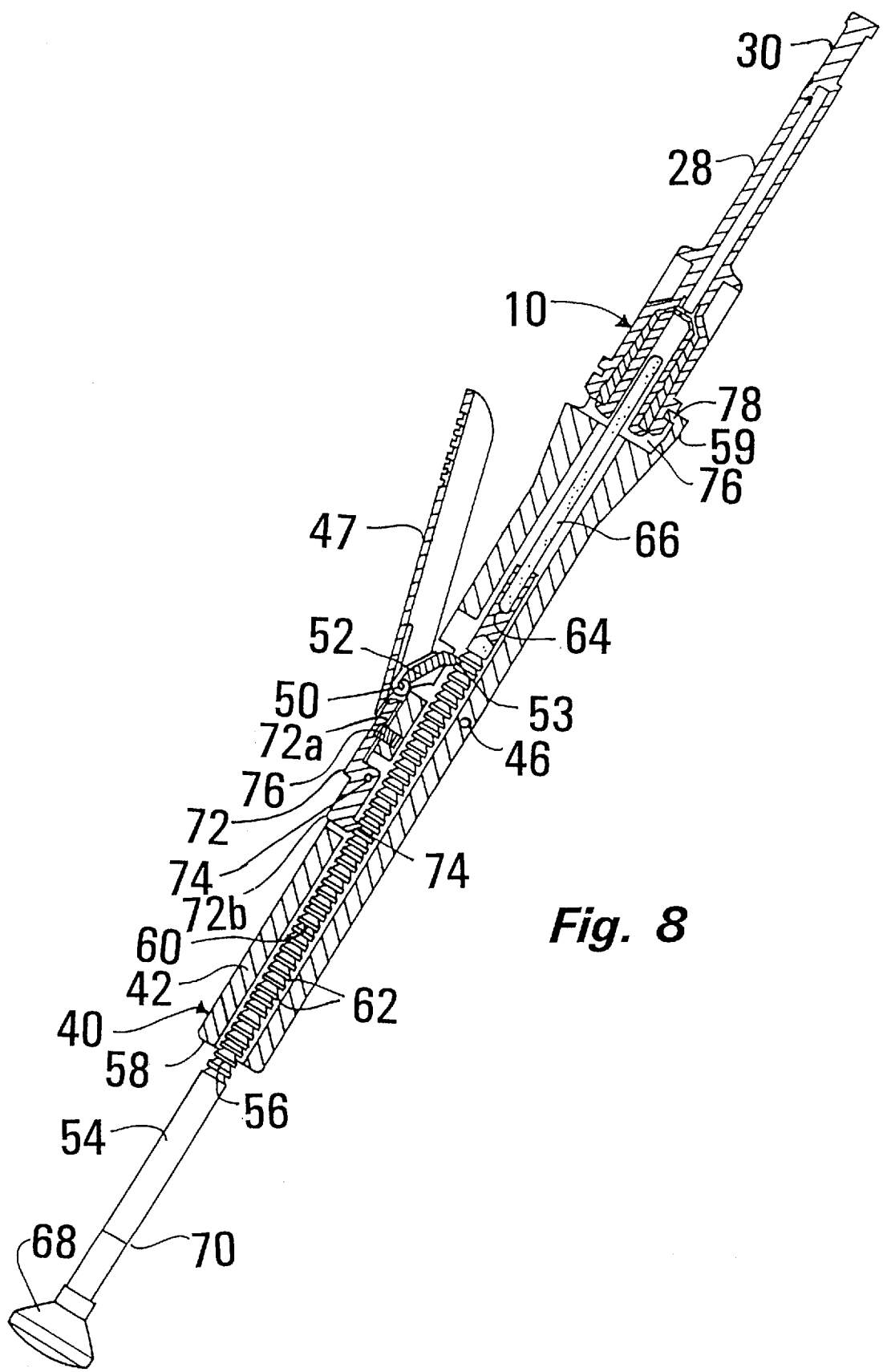
FIG. 8 is a longitudinal sectional view of the applicator and capsule of FIG. 7 prior to commencement of dispensing.
Figure 9:
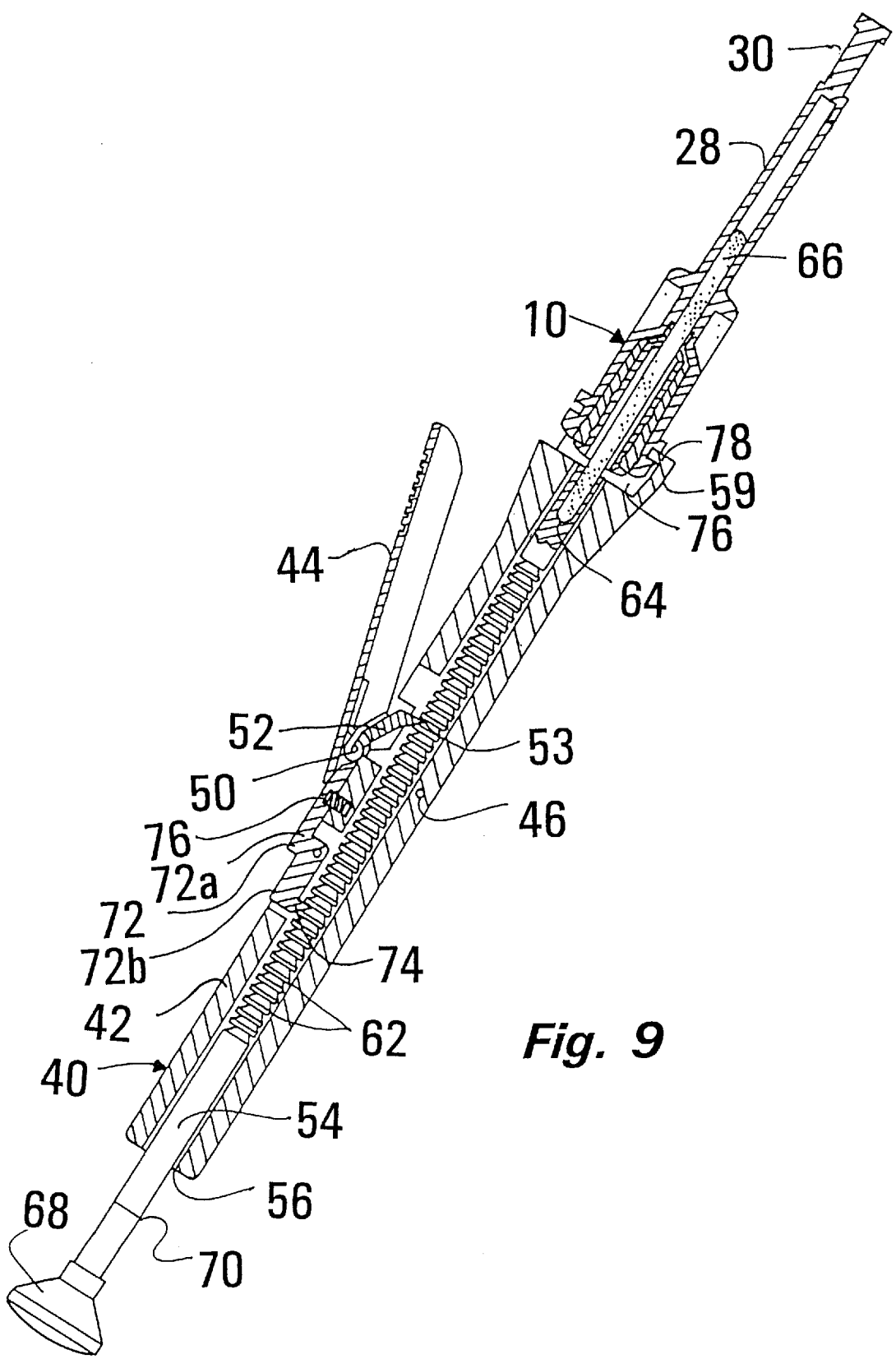
FIG. 9 is a view similar to FIG. 8 showing the applicator and capsule in a condition ready to commence dispensing.
Figure 10:
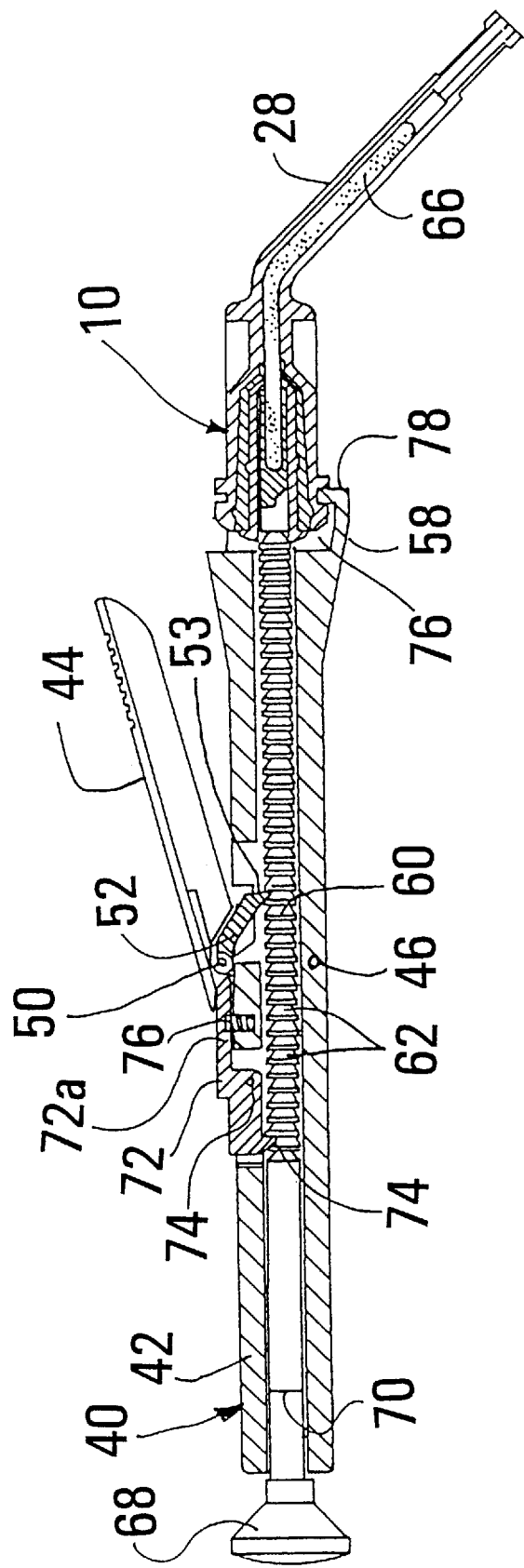

In the unactivated condition of the capsule 10 shown in FIGS. 2 and 5, the initial location of the plunger 20 is determined by a locating ring 24 (see FIG. 5) which extends around the periphery of the plunger 20.

As can be seen in FIG. 5, the plunger 20 is initially disposed so that the locating ring 24 is disposed adjacent the end 13 remote from the partition 17. Further, the plunger 20 has a head 25 at the end thereof remote from the body 12 in the unactivated condition.

The second compartment 18 is partially located within the body 12 and partially in an elongated conduit 28 which extends away from the body 12 and is of lesser external dimension than the body 12. A transverse connecting portion 29 extends between the body 12 and the conduit 28. The second compartment 18 has an inner end sealed by the partition 17 in the unactivated condition of the capsule 10 and an outer end sealed by an integrally formed plug 30. The second compartment 18 contains a quantity of dental alloy in particulate form. As can be seen in FIGS. 3 and 4 and FIGS. 5 and 6, the internal diameter of the compartment 18 is less than that of the compartment 16.

Figure 6:
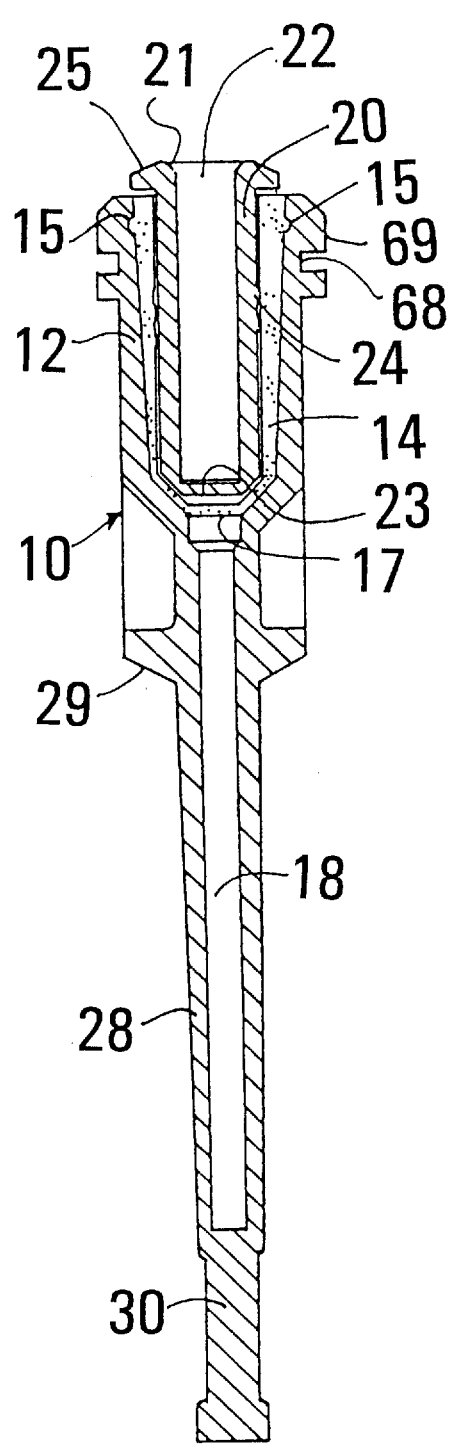
FIG. 6 is a vertical section through the capsule as shown in FIG. 2 along the lines X—X of FIGS. 3 and 4.

In operation, an operator pushes the plunger 20 into the body 12 until the head 25 is in contact with the body 12 as shown in FIGS. 2 and 6. This action firstly pushes the mercury in the compartment 16 against the partition 17 and hydraulic pressure applied by the mercury ruptures the partition 17. Continued depression of the plunger 20 expels the mercury from the compartment 16. The partition 17 may be an integral part of the capsule 10 or it may be a separate member formed of a plastics or metallic foil affixed in place by any suitable means. The partition 17 is broken under hydraulic pressure from the mercury as applied to the mercury by the plunger 20. The plunger 20 has an interference fit with the sides of the container 14 so that no mercury can escape past the plunger 20. As the plunger 20 is depressed, the locating ring 24 is pushed along the sides of the mercury container 14 and in this connection, the mercury container 14 is preferably formed of relatively soft material so as to accommodate the ring 22 by deformation. The depression of the plunger 20 and the breaking of the partition 17 and the continued depression of the plunger 20 causes the mercury to be expelled from the compartment 16 into the compartment 18 to contact the alloy powder in the compartment 18.

Preferably, the partition 17 is such that it breaks in a petal like formation and the petals are conveniently folded into a slight recess (not shown) in the walls of the interior of the body 10. The breaking of the partition 17 into a petal like formation may be facilitated by forming lines of weakness in the partition 17. These lines of weakness may simply be portions which are relatively thin compared to the rest of the partition 17 and may have a thickness of, for example, 0.1 to 0.2 mm. Preferably, the lines of weakness are formed in a cross.

The retention of the broken portion of the partition 17 on the interior walls is preferable to having a partition 17 which is broken away from the wall of the chamber upon activation because the non-broken away partition 17 does not become mixed with the amalgam. Further, as can be seen in FIGS. 5 and 6 the partition 17 preferably has a central portion generally at 90° to the axis of the capsule which central portion contains the line of weakness, and a first peripheral ring which surrounds the central portion and is disposed at an acute angle to a plane running through the central portion of the partition 17. Further, the membrane 23 is preferably of similar shape having a central portion generally at 90° to the axis of the capsule flanked by a second peripheral ring which is disposed at an acute angle to a plane running through the central portion of the membrane 23. However, it is preferred that the outer angle of the second peripheral ring be slightly less than the acute angle of the first peripheral ring as it is found that this leads to more efficient expulsion of the mercury from the compartment 16.

After this operation has been accomplished the capsule 10 can be placed in a high speed amalgamator and triturated for as long as is necessary to produce a homogeneous amalgam in the compartment 18 after the plunger 20 has been depressed. It is found that certain types of amalgam such as dispersed alloy containing amalgams will not mix readily in the restricted space provided by the elongated compartment 18. However, certain amalgams having a highly reactive surface area and not requiring a high energy input for amalgamation such as "LOJIC PLUS, LOJIC AND PERMITE" produced by the assignee of the present invention will mix in the compartment 18.

After the mixing process the capsule 10 may be placed in an applicator such as that shown in FIGS. 7 to 10. Conveniently, the conduit 28 is flexible so that it can be supplied straight as shown in FIGS. 1 to 6 but can be readily bent by the dentist to any convenient configuration. This is conveniently done by a bending tool. Further, the plug 30 has to be broken off before dispensing of amalgam can take place. In this connection the plug 30 preferably has a frangible portion (not shown) to facilitate it being broken off at the outer end of the compartment or mixing chamber 18.

However, it is to be understood that the conduit 28 could be rigid and supplied in any already bent configuration to the dentist.

In FIGS. 7 to 10 of the accompanying drawings there is shown an applicator 40 comprising an elongated hollow, generally cylindrical body member 42. The body member 42 comprises an intermediate portion 43 with flat sides. A lever 44 is pivotally connected to the body member 42 at the intermediate portion 43.

The lever 44 has an inner end which pivots about a pin 46, in use. The inner end of the lever 44 is formed with a pair of depending spaced apart plates 47 (see FIG. 7) which are disposed externally of respective flat sides of the intermediate portion 43. The pin 46 extends through opposed apertures in the plates 47 and through the intermediate portion 43.

Figure 15:
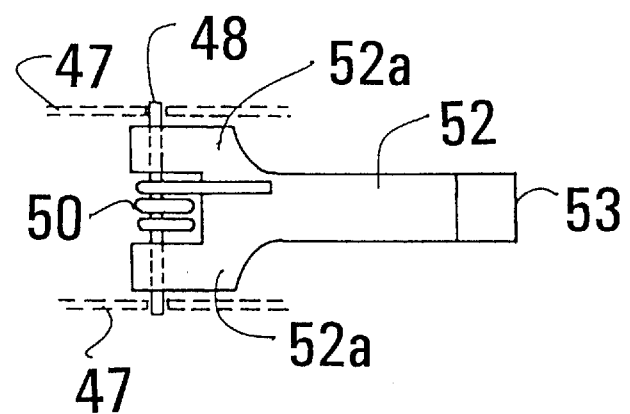
FIG. 15 is a plan view of a pawl of the applicator of FIGS. 7 to 10.

There is an additional pin 48 which extends between a further pair of opposed apertures in the plates 47 above the body member 42 as seen in FIGS. 7 to 10. A coil spring 50 (see FIGS. 8 to 10) is mounted about the pin 48 between the plates 47. The coil spring 50 has a first free end which bears against the lever 44 and a second free end which bears against a pawl member 52. The pawl member 52 has a forked inner end with apertured legs 52a mounted about the pin 48 and with the coil spring 50 located between the legs as shown in FIG. 15. The free ends of the coil spring 50 are biased outwardly and normally urge the lever 44 and the pawl 52 apart. The pawl member has an outer end provided with a tooth 53.

The applicator 40 also comprises an inching mechanism comprising an elongated rod 54. The rod 54 enters the body member 42 through an aperture 56 in a trailing end 58 hereof. The body member 42 also has a leading end 59 configured to receive the capsule 10 as will be described. The rod 54 comprises an intermediate ratchet portion 60 formed with a plurality of teeth 62 in succession. Each of the teeth 62 has a steep face facing the trailing end 58 and an opposed less steep face facing the leading end 59. The teeth 62 are engaged in turn by the tooth 53 of the pawl 52. The rod 54 has a forward end adjacent the leading end 59 of the body member 42 which forward end contains a co-axial recess 64 arranged to receive releasably a pusher rod 66. The pusher rod 66 is formed of a material such that it is a longitudinally rigid whilst being transversely flexible.

This enables the pusher rod 66 to push amalgam through the conduit 28 even when the conduit is curved as will be described. The pusher rod 66 may be engaged with the rod 54 by being a snug fit in the recess 64 but it can be engaged by any other convenient means such as by being threadedly engaged with the recess 64. However, it is preferred that the pusher rod 66 simply have a snug, push fit in the recess 64 which enables the pusher rod 66 to be released from the recess 64 once a capsule 10 has been used so that the pusher rod 66 remains inside the capsule.

The rod 54 also has a trailing end adjacent the end 58 of the body member 42. The trailing end of the rod 54 is provided with a knob 68 and one or more position marking circumferential grooves 70.

The body member 42 further comprises a stop member in the form of a stepped plate 72 which is pivotally mounted about pin 74 which extends through the body member 42 to the ear of the pin 46. The stepped plate 72 has a leading portion 72a and a trailing portion 72b. The leading portion 72a has a leading end located between the inner end of the lever 44 and the body member 42 and the trailing portion 72b has a trailing end located within a recess in the body member 42. The trailing portion 72b of the stepped plate 72 has a depending tooth 74 at the trailing end thereof which tooth 74 engages with the teeth 62 of the ratchet portion 60. The tooth 74 is shaped so that one side is inclined to conform to a leading edge of one tooth 62 and the other side is orientated so as to conform to the trailing edge of the next leading tooth 62. Further, a coil spring 76 is mounted between the body member 42 and the leading portion 72a of the stepped plate 72 and is mounted in respective opposed apertures in these members. The coil spring 76 normally urges the body member 42 and the leading portion 72a of the stepped plate 72 apart such that the stepped plate 72 is pivoted about the pin 74 and the tooth 74 is firmly in engagement with the ratchet 60.

Figure 11:
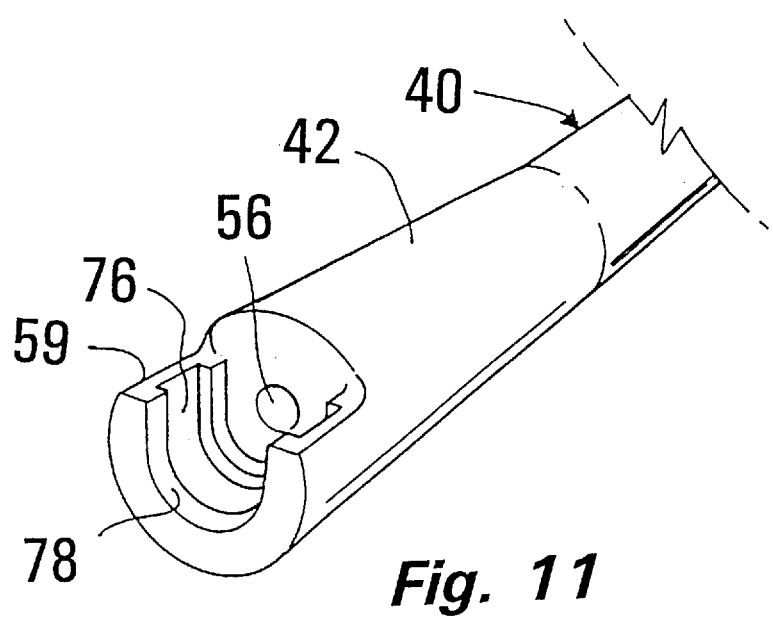
FIG. 11 is a perspective view of a leading end of the applicator of FIGS. 7 to 10 without a capsule in place.

The capsule 10 described above has a widened portion adjacent the end 13 which widened portion has a circumferential groove 68 and associated circumferential rib 69 at the end thereof adjacent the plunger 20. In use, the rib 69 is engaged with a part circular recess 76 at the leading end 59 of the body member 42 whilst the groove 68 engages with an outer, part circular rib 78. The recess 76 and the rib 78 can best be seen in FIGS. 11 whilst the engagement of the groove 68 and the rib 69 with the recess 76 and the rib 78 can best be seen in FIGS. 8 to 10. Once the capsule 10 has been loaded the system is in the configuration shown in FIGS. 7 and 8. The operator then presses the lever 44 towards the cylindrical member 42. This pivots the lever 44 about the pin 46 and so causes the pawl 52 to push forwardly by means of the bolt 53 against the leading tooth 62 of the ratchet member 62 and push the inching mechanism forward by an increment. Simultaneously, the leading portion 72a of the plate 72 is depressed so that the tooth 74 rides up the leading face of the trailing tooth 62 with which it is in contact. This action of the pawl 52 and the plate 72 pushes the rod 54 and hence the pusher rod 66 forward by an increment into the recess 21 of the plunger 20. This action is repeated until the pusher rod 66 contacts the membrane 23 of the hollow plunger 20.

This is indicated to the operator by alignment of a groove 70 with the trailing end 58 of the body member 42. Upon further depressions of the lever 44 and corresponding incremental movement of the rod 54 the pusher rod 66 breaks through the membrane 23 of the plunger 20 and then passes the ruptured partition 17 at the inner end of the first compartment 16 to enter the second compartment 18. This incremental movement of the rod 54 and the pusher rod 66 is continued until the operator senses back pressure which indicates that the amalgam in the second compartment 18 has been pushed to the far end of the second compartment 18 of the capsule 10 adjacent the frangibly mounted plug 30. For filling of most cavities the conduit 28 has to be bent by the dentist prior to the breaking off of the plug 30.

The particular degree of bend employed will vary from case to case.

Figure 13:
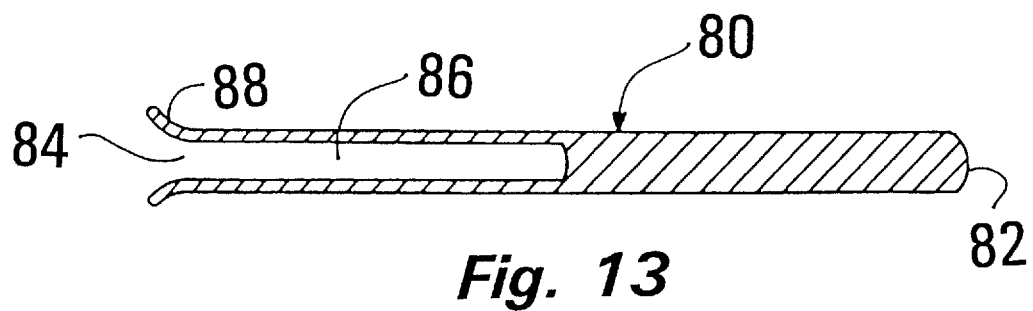
FIG. 13 is a longitudinal section through the bending tool of FIG. 12.
Figure 12:
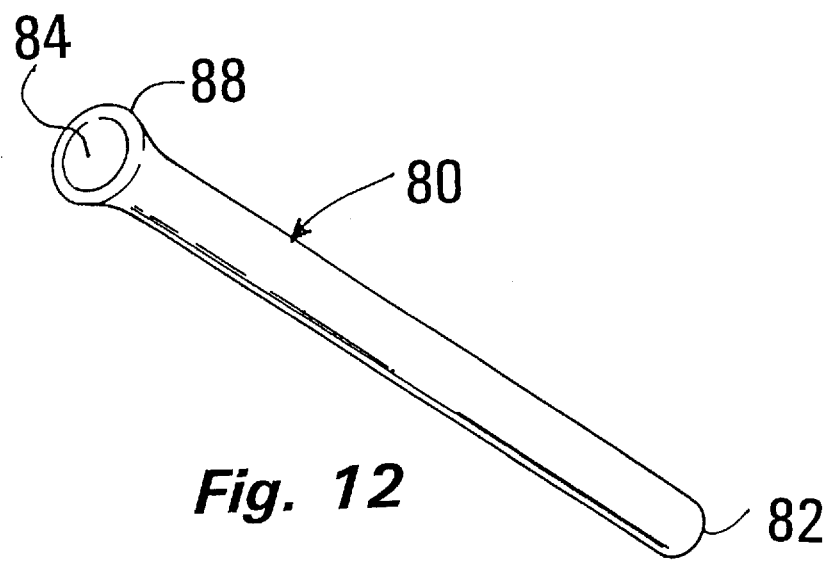
FIG. 12 is a perspective view of a bending tool for use with the capsule of FIGS. 1 to 6.

The bending may conveniently be effected by a tool 80 shown in FIGS. 12 and 13. As can be seen the tool 80 is elongated tool has a first closed end 82 and a second open end 84. A co-axial recess 86 extends from the end 84 partially along the length of the tool 80 as seen in FIG. 13 for a length greater than that of the conduit 28. Further, the open end 84 has an outwardly flared outer portion 88.

Figure 14:
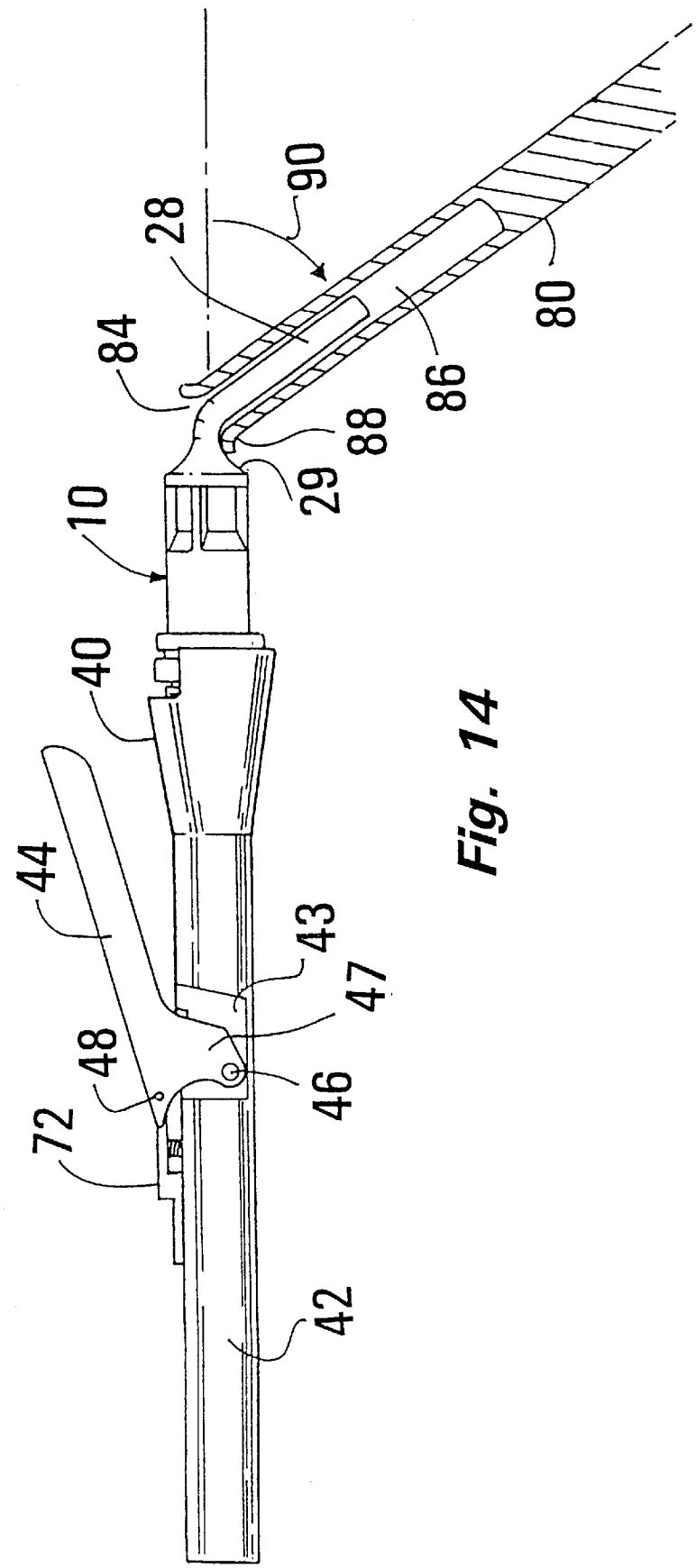
FIG. 14 is a side elevation of a leading portion of the applicator of FIGS. 7 to 10, with a capsule of FIGS. 1 to 6 in place showing the bend tool of FIGS. 12 and 13 in operation.

The tool 80 is used by placing the end 84 over a conduit 28 of a capsule 10 in an applicator 40 as shown in FIG. 14. The tool 80 is pushed onto the conduit 28 until the end 84 engages with the transverse connecting portion 29 and the conduit 28 enters the recess 86. With the end 84 in engagement with the portion 29 the dentist then rotates the tool 80 about the point of engagement with the portion 29 in the direction of an arrow 90 so as to bend the conduit to a desired angle which may be as much as 90° or more from the original alignment of the conduit 28. The flared end 86 is preferred because it is found that this reduces any tendency of the end 84 to cut into the conduit 28 during the bending operation.

Once the bending operation is complete the frangibly mounted plug 30 is broken off.

The dentist can now apply the amalgam directly into a cavity of a tooth being restored by further incremental movement of the rod 54 and the pusher rod 66 using the lever 44. The amalgam is typically pushed out in incremental amounts until the dentist has filled the cavity.

Thus, the applicator 40 is designed so that the ratchet member 62 is moved an incremental distance upon each movement of the lever 44. At each incremental movement the tooth 74 rides over the next trailing tooth 62 and engages behind it.

Upon release of the lever 44, the coil spring 50 urges the lever 44 away from the cylindrical member 42. The engagement of the tooth 76 with the teeth 62 prevents the rod 54 from moving inadvertently rearward.

The dentist can insert one or more quantities of amalgam into the cavity of the tooth before commencing condensation or he may commence condensation and then insert a further quantity of amalgam into the cavity as required.

The application procedure can be repeated until the leading end of the pusher rod 66 is adjacent the free end of the conduit 28 from which the plug 30 was broken off. At this point substantially all of the amalgam has been used. The capsule 10 can then be discarded. Preferably, the capsule 10 is simply detached from engagement with the rib 78 and the pusher rod 66 remains inside the capsule 10. This may be achieved by lifting the lever 44 so as to depress the leading portion 72*a* of the plate 72 and raise the trailing portion 72*b* so that the tooth 74 is no longer in engagement with any of the teeth 62. Then the rod 54 can be removed from the rearward end 58 of the body member 42. As the conduit 28 is by now typically bent there is a sufficient degree of engagement of the pusher rod 66 with the interior of the capsule 10 to enable the pusher rod 66 to remain in the capsule 10 as the rod 54 is removed.

Further, the plug 30 is preferably configured so that it can be inserted in the recess 22 once the capsule 10 has been used. In this way the used capsule 10 is sealed and escape of residual mercury is reduced.

The second compartment 18 is designed so that it contains no constrictions and is of substantially the same size and shape throughout so that no effort is required to push the amalgam therethrough. However, it is preferred that the second compartment 18 have a slight outward taper from the partition 17 to the outer end from which the plug 30 is broken off as it is found that the slight outward taper reduces the possibility of the amalgam packing in the conduit 28. It is essential to avoid even slight reductions in cross section of the conduit 28 to avoid packing of the amalgam in the conduit 28.

Preferably, the second compartment 18 which constitutes the mixing chamber in the embodiment described, has an internal diameter from b 1to 3.5 mm, more preferably from 2 to 3 millimeters. A conduit 28 of larger diameter would be difficult to insert into a tooth cavity. For some applications such as filling small cavities, which are found frequently in children's teeth, the second compartment 18 may have an internal diameter of about 1 to 1.5 millimeters.

Further, the conduit 28 preferably has a length in the range from 15 to 50 mm, more preferably from 15 to 40 mm, yet more preferably from 20 to 30 mm.

The mixing chamber 18 is preferably from 20 to 60 mm in length, more preferably from 30 to 40 mm in length.

The capsule of the present invention can be manufactured from plastics material by being moulded. The body 12 is preferably relatively rigid, the plunger 20 is preferably relatively rigid whilst the mercury container 14 is preferably formed of a relatively soft polyethylene material.

Figure 16:
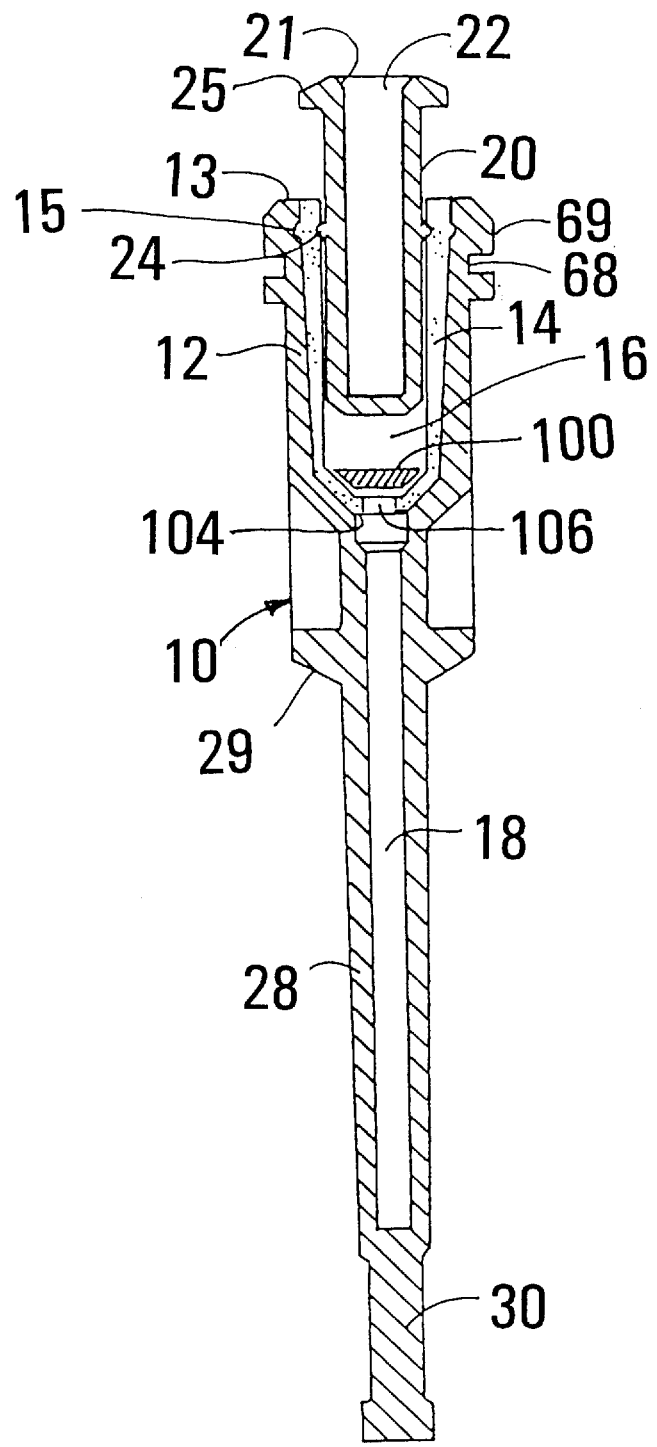
FIG. 16 is a view similar to FIG. 5 showing an alternative embodiment of a capsule in accordance with the present invention.

Modifications and variations such as would be apparent to a skilled addressee are deemed within the scope of the present invention. For example, the activation system of the capsule can take many forms other than that described herein. In particular, the mercury could be contained in a sealed flexible bag and means be provided for rupturing the flexible bag to enable the mercury to contact the amalgam alloy powder. Such an arrangement is shown in FIG. 16 in which like reference numerals denote like parts. In FIG. 16, the compartment 16 contains a sachet of mercury 100 which rests on an intervening wall 104. The wall 104 in this embodiment contains an aperture 106. The sachet 100 and the wall 104 in this embodiment form together a partition which keeps apart the mercury and alloy powder. The plunger 20 when depressed upturns the sachet of mercury 100 and the mercury is squared through the aperture 106 into the first compartment 18. Subsequently, the procedure is as described above for the capsule of FIGS. 1 to 4.

Further, the applicator 40 described herein is arranged to be manually operated. However, it is envisaged that the applicator 40 could be pneumatically, electronically or electrically powered so that a piston device is operated by a worm drive or the like. Further, the applicator 40 could be pneumatically powered off the dentists standard air supply such as by means of a foot control.

Still further, the pusher rod 66 could be replaced by an equivalent member such as a coil spring with a head on it.

I claim:

1. A dental composition capsule comprising a body and a conduit extending from the body, a first chamber within said body, part of said first chamber comprising a mixing chamber extending along the length of said conduit and being free of constrictions along its entire length, said body and said conduit arranged to contain liquid metal and particulate dental alloy in separated condition, said conduit having an outlet end, means for enabling the liquid metal and the particulate dental alloy to contact one another in said mixing chamber and to be formed into a composition, said conduit having a lesser external dimension than said body, a longitudinally rigid and transversely flexible pusher member located adjacent said mixing chamber and arranged for being moved therethrough for dispensing composition from said conduit at said outlet end.

2. A dental composition capsule as defined in claim 1 wherein said conduit is flexible and has a memory for retaining said conduit in bent condition during use.

3. A dental composition capsule as defined in claim 2 wherein said flexible pusher member conforms to said conduit in its bent condition.

4. A dental composition capsule as defined in claim 3 wherein said mixing chamber has a length in the range of 30 to 40 millimeters.

5. A dental amalgam capsule comprising a body and a conduit extending from the body, a first chamber within said body and said conduit arranged to contain mercury and particulate dental alloy in separated condition, a part of said first chamber comprising a mixing chamber extending along the length of said conduit and being free of constrictions along its entire length, said conduit having an outlet end, means for enabling the mercury and the particulate dental alloy to contact one another in said mixing chamber and to be formed into an amalgam, said conduit having a lesser external dimension than said body, and a longitudinally rigid and transversely flexible member movable through said mixing chamber for dispensing amalgam from said outlet end of said conduit.

6. A dental amalgam capsule as defined in claim 5 wherein said conduit is flexible and has a memory for retaining said conduit in bent condition during use.

7. A dental amalgam capsule as defined in claim 6 wherein said flexible pusher member conforms to said conduit in its bent condition.

8. A dental amalgam capsule as defined in claim 7 wherein said mixing chamber has a length in the range of 30 to 40 millimeters.

* * * * *